(12) United States Patent
BaMaung et al.

(10) Patent No.: US 7,030,262 B2
(45) Date of Patent: Apr. 18, 2006

(54) 3-AMINO-2-HYDROXYALKANOIC ACIDS AND THEIR PRODRUGS

(75) Inventors: Nwe Y. BaMaung, Niles, IL (US);
Richard A. Craig, Racine, WI (US);
Jack Henkin, Highland Park, IL (US);
Megumi Kawai, Libertyville, IL (US);
Xenia B. Searle, Grayslake, IL (US);
George S. Sheppard, Wilmette, IL (US); Jieyi Wang, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 66 days.

(21) Appl. No.: 10/635,342

(22) Filed: Aug. 6, 2003

(65) Prior Publication Data

US 2004/0122098 A1 Jun. 24, 2004

Related U.S. Application Data

(60) Provisional application No. 60/401,317, filed on Aug. 6, 2002.

(51) Int. Cl.
*C07C 331/00* (2006.01)

(52) U.S. Cl. .................. 560/19; 560/155; 562/433; 562/553

(58) Field of Classification Search .................. 560/19, 560/155; 562/433, 553, 453; 514/562
See application file for complete search history.

(56) References Cited

U.S. PATENT DOCUMENTS 6,242,494 B1 * 6/2001 Craig et al. .................. 514/613
2002/0002152 A1 1/2002 Craig et al.

FOREIGN PATENT DOCUMENTS

WO 99/57098 11/1999

OTHER PUBLICATIONS

Kaji et al, Bull. Chem. Soc Jpn, 49, pp 3181-3184 (1976);
Rich et al, Journal of Org. Chem., 45, pp 2288-2290 (1980).*
Matsuda et al, Bull. Chem. Soc. Jpn. 655 (2) pp 360-365 (1992); Peet et al, J. Med. Chemistry, 33(1) pp 394-407 (1990).*
Ojima et al, Tetrahedron Letters, 33 (39) pp5537-5700 (1992).*
Peet et al, J. Med. Chemistry, 33(1) pp 394-407 (1990).*
Craig, et al., Chemical Abstract. Database accession No. 135:3311987 CA, XP002262659.
Database Crossfire Beilstein, Database accession No. brn 5486092, XP002262661; Tetrahedron Letters 33(39):5737-5740 (1992).
Database Crossfire Beilstein. Database accession No. brn 3650004, XP002262660; Tetrahedron Letters 34(47):7557-7560 (1993).
Database Crossfire Beilstein. Database accession No. brn 4803192, XP02262662; Bull. Chem. Soc. Jpn. 65(2):360-365 (1992).
Database Crossfire Beilstein. Database accession No. brn 1721653, XP002262663; Chem Zentralbl 77(11):765 (1906).
Database Crossfire Beilstein. Database accession No. brn 2430446, XP002262664; Bull. Chem. Soc. Jpn. 49:3181-3184 (1976).
Database Crossfire Beilstein. Database accession No. brn 2968669, XP002262665: J. Med. Chem. 33(12):394-407 (1990).
Database Crossfire Beilstein. Database accession No. brn 2970752, XP002262666; J. Med. Chem. 33(1):694-407 (1990).
Database Crossfire Beilstein. Database accession No. brn 3536828, XP002262667; J. Med. Chem. 33(1):694-407 (1990).
Database Crossfire Beilstein. Database accession No. brn 3609285, XP002262668; Tetrahedron 48(10):1853-1868 (1992).
Database Crossfire Beilstein. Database accession No. brn 4230470, XP002262669; J. Org. Chem. 45(12):2288-2290 (1980).

(Continued)

*Primary Examiner*—Ceila Chang
*Assistant Examiner*—Hector M. Reyes
(74) *Attorney, Agent, or Firm*—B. Gregory Donner

(57) ABSTRACT

Compounds having the formula

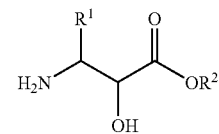

are useful for treating conditions which arise from or are exacerbated by angiogenesis. Also disclosed are pharmaceutical compositions comprising the compounds, methods of treatment using the compounds, methods of inhibiting angiogenesis, and methods of treating cancer.

4 Claims, No Drawings

OTHER PUBLICATIONS

Database Crossfire Beilstein. Database accession No. brn 4231872, XP002262670; Bioorg. Med. Chem. Lett. 10(20): 2305-2310 (2000).

Database Crossfire Beilstein. Database accession No. brn 5486837, XP00226267;Tetrahedron Lett. 33(39):5737-5740 (1992).

Database Crossfire Beilstein. Database accession No. brn 5740104, XP002262672; J. Org. Chem. 50(1):91-97 (1985).

Database Crossfire Beilstein. Database accession No. brn 5862099, XP002262673; Tetrahedron Lett. 34(3):504-504 (1993).

Database Crossfire Beilstein. Database accession No. brn 5906442, XP002262674; Tetrahedron Lett. 34(8):1247-1250 (1993).

Database Crossfire Beilstein. Database accession No. brn 6592217, XP002262675; Tetrahedron Lett. 34(47):7557-7560 (1993).

Database Crossfire Beilstein. Database accession No. brn 6844111, XP002262676; Tetrahedron: Asymmetry 5(2): 203-206 (1994).

Database Crossfire Beilstein. Database accession No. brn 7566877, XP002262667; J. Antibiot. 49(9):890-899 (1996).

Griffith et al., "Methionine aminopeptidase (type 2) is the common target for angiogenesis inhibitors AGM-1470 and ovalicin", Chemistry and Biology 4(6):461-471 (1997).

Sin et al., "The anti-angiogenic agent fumagillin covalently binds and inhibits the methionine aminopeptidase, MetAP-2", Proc. Natl. Acad. Sci. USA 94:6099-6103 (1997).

* cited by examiner

3-AMINO-2-HYDROXYALKANOIC ACIDS AND THEIR PRODRUGS

This application claims priority to U.S. Provisional Patent Application Ser. No. 60/401,317, filed Aug. 6, 2002.

TECHNICAL FIELD

The present invention relates to novel compounds having methionine aminopeptidase-2 inhibitory (MetAP2) activity useful for treating conditions which arise from or are exacerbated by angiogenesis, pharmaceutical compositions comprising the compounds, methods of treatment using the compounds, methods of inhibiting angiogenesis, and methods of treating cancer.

BACKGROUND OF THE INVENTION

Angiogenesis is the fundamental process by which new blood vessels are formed and is essential to a variety of normal body activities (such as reproduction, development, and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days.

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. Thus, there is a continuing need for compounds which demonstrate antiangiogenic activity.

SUMMARY OF THE INVENTION

In its principle embodiment, the present invention provides a compound of formula (I)

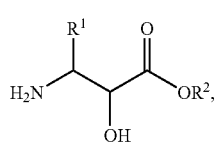

(I)

or a therapeutically acceptable salt thereof, wherein $R^1$ is selected from the group consisting of alkyl, alkylsulfanylalkyl, aryl, arylalkyl, cycloalkyl, (cycloalkyl)alkyl, (heterocycle)alkyl, and hydroxyalkyl; and $R^2$ is selected from the group consisting of hydrogen, alkenyl, alkyl, alkylcarbonyloxyalkyl, alkylcarbonylalkyl, aryl, arylalkyl, cycloalkyl, (cycloalkyl)alkyl, heterocycle, and (heterocycle)alkyl.

In another embodiment, the present invention provides a pharmaceutical composition comprising a compound of formula (I), or a therapeutically acceptable salt thereof, in combination with a therapeutically acceptable carrier.

In another embodiment, the present invention provides a method of inhibiting angiogenesis in a mammal in recognized need of such treatment comprising administering to the mammal a pharmaceutically acceptable amount of a compound of formula (I).

In another embodiment, the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

As used herein, the singular forms "a", "an", and "the" include plural reference unless the context clearly dictates otherwise.

As used in the present specification the following terms have the meanings indicated:

The term "alkenyl," as used herein, refers to a monovalent straight or branched chain group of one to ten carbon atoms containing at least one carbon-carbon double bond.

The term "alkoxy," as used herein, refers to an alkyl group attached to the parent molecular moiety through an oxygen atom.

The term "alkyl," as used herein, refers to a group derived from a straight or branched chain saturated hydrocarbon of one to ten atoms.

The term "alkylcarbonyl," as used herein, refers to an alkyl group attached to the parent molecular moiety through a carbonyl group.

The term "alkylcarbonyloxy," as used herein, refers to an alkylcarbonyl group attached to the parent molecular moiety through an oxygen atom.

The term "alkylcarbonyloxyalkyl," as used herein, refers to an alkylcarbonyloxy group attached to the parent molecular moiety through an alkyl group.

The term "alkylsulfanyl," as used herein, refers to an alkyl group attached to the parent molecular moiety through a sulfur atom.

The term "alkylsulfanylalkyl," as used herein, refers to an alkylsulfanyl group attached to the parent molecular moiety through an alkyl group.

The term "amino," as used herein, refers to $-NR^aR^b$, wherein $R^a$ and $R^b$ are independently selected from the group consisting of hydrogen, alkyl, alkylcarbonyl, cycloalkyl, (cycloalkyl)alkyl, and unsubstituted aryl.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkoxy, alkyl, alkylcarbonyl, amino, carboxy, cyano, halo, haloalkoxy, haloalkyl, nitro, and oxo.

The term "arylalkyl," as used herein, refers to an aryl group attached to the parent molecular moiety through an alkyl group. The alkyl part of the arylalkyl can be optionally substituted with an amino group.

The term "carbonyl," as used herein, refers to —C(O)—.

The term "carboxy," as used herein, refers to —CO$_2$H.

The term "cyano," as used herein, refers to —CN.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to twelve carbon atoms. Examples of cycloalkyl groups include, but are not limited to, cyclopropyl, cyclopentyl, bicyclo [3.1.1]heptyl, and adamantyl.

The term "(cycloalkyl)alkyl," as used herein, refers to a cycloalkyl group attached to the parent molecular moiety through an alkyl group.

The term "halo," or "halogen," as used herein, refers to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "heterocycle," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to a phenyl group, a monocyclic cycloalkenyl group, as defined herein, a monocyclic cycloalkyl group, as defined herein, or another monocyclic heterocycle group, as defined herein; and tricyclic groups in which a bicyclic system is fused to a phenyl group, a monocyclic cycloalkenyl group, as defined herein, a monocyclic cycloalkyl group, as defined herein, or another monocyclic heterocycle group. The heterocycle groups of the present invention can be attached to the parent molecular moiety through a carbon atom or a nitrogen atom in the group. Examples of heterocycles include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocycle groups of the present invention can be optionally substituted with one, two, three, four, or five substituents independently selected from the group consisting of alkoxy, alkyl, alkylcarbonyl, amino, carboxy, cyano, halo, haloalkoxy, haloalkyl, nitro, and oxo.

The term "(heterocycle)alkyl," as used herein, refers to a heterocycle group attached to the parent molecular moiety through an alkyl group.

The term "nitro," as used herein, refers to —NO$_2$.

The term "oxo," as used herein, refers to =O.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood. Prodrugs of the present invention are compounds of formula (I) where $R^2$ is other than hydrogen (i.e., carboxylic esters). Representative prodrugs include, but are not limited to, methyl (3R)-3-amino-2-hydroxy-5-(methylsulfanyl)pentanoate; methyl (2RS,3R)-3-amino-4-cyclohexyl-2-hydroxybutanoate; (1S,2R)-2-amino-2,3-dihydro-1H-inden-1-yl (2RS,3R)-3-amino-4-cyclohexyl-2-hydroxybutanoate; benzyl (2S,3R)-3-amino-3-cyclopentyl-2-hydroxypropanoate; benzyl (2S,3R)-3-amino-3-cycloheptyl-2-hydroxypropanoate; (2S)-2-(methylamino)-2-(1-naphthyl)ethyl (2S,3R)-3-amino-5-(ethylsulfanyl)-2-hydroxypentanoate; (2R)-2-(methylamino)-2-(1-naphthyl)ethyl (2S,3R)-3-amino-5-(ethylsulfanyl)-2-hydroxypentanoate; 2-(methylamino)-2-(1-naphthyl)propyl (3R)-3-amino-5-(ethylsulfanyl)-2-hydroxypentanoate; (2R)-2-(methylamino)-2-(1-naphthyl)ethyl (2S,3R)-3-amino-4-cyclohexyl-2-hydroxybutanoate; (2R)-2-(methylamino)-2-(1-naphthyl)ethyl (2S,3R)-3-amino-2-hydroxy-5-phenylpentanoate; methyl (2RS,3R)-3-amino-5-(ethylsulfanyl)-2-hydroxypentanoate; benzyl (2RS,3R)-3-amino-5-(ethylsulfanyl)-2-hydroxypentanoate; butyl (2RS,3R)-3-amino-5-(ethylsulfanyl)-2-hydroxypentanoate; isopropyl (2S,3R)-3-amino-2-hydroxy-5-(isopropylsulfanyl)pentanoate; isopropyl (2RS,3R)-3-amino-5-(ethylsulfanyl)-2-hydroxypentanoate; [(2,2-dimethylpropanoyl)oxy]methyl (2RS,3R)-3-amino-5-(ethylsulfanyl)-2-hydroxypentanoate; sec-butyl (2RS,3R)-3-amino-5-(ethylsulfanyl)-2-hydroxypentanoate; (1,3-dioxo-1,3-dihydro-2H-isoindol-2-yl)methyl (2RS,3R)-3-amino-5-(ethylsulfanyl)-2-hydroxypentanoate; sec-butyl (2RS,3R)-3-amino-2-hydroxy-5-(isopropylsulfanyl)pentanoate; [(2,2-dimethylpropanoyl)oxy]methyl (2S,3R)-3-amino-2-hydroxy-5-(isopropylsulfanyl)pentanoate; (1,3-dioxo-1,3-dihydro-2H-isoindol-2-yl)methyl (2S,3R)-3-amino-2-hydroxy-5-(isopropylsulfanyl)pentanoate; and 3-oxo-1,3-dihydro-2-benzofuran-1-yl (2S,3R)-3-amino-2-hydroxy-5-(isopropylsulfanyl)pentanoate.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit angiogenesis. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrastemal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The antiangiogenic effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets, and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

*Proc. Natl. Acad. Sci. USA* 94: 6099–6103 (1997) and *Chemistry and Biology*, 4(6): 461–471 (1997) report that both AGM-1470 and ovalicin, a sequiterpene isolated from the fungus *Pseudorotium ocalis* have been found to bind to a common bifunctional protein, type 2-methionine aminopeptidase (MetAP-2) and conclude that MetAP2 plays a critical role in the proliferation of endothelial cells and may serve as a promising target for the development of new anti-angiogenic drugs.

Assays for the inhibition of catalytic activity of MetAP2 were performed in 96-well microtiter plates. Compounds to be tested (compounds of formula (I) where $R^2$ is hydrogen) were dissolved in dimethyl sulfoxide at 10 mM and diluted ten-fold in assay buffer (50 mM HEPES, pH 7.4, 100 mM NaCl). Ten microliters of solution of each compound to be tested for inhibition were introduced into each cell of the plate. Zero inhibition of enzyme activity was taken to be the result obtained in cells in which 10 mL of assay buffer was placed. A mixture totaling 90 mL per well and made up of 84 mL of assay buffer containing 100 mM $MnCl_2$, 1 mL of L-amino acid oxidase (Sigma Catalog No. A-9378, ~11 mg/mL), 1 mL of horseradish peroxidase (Sigma Catalog No. P-8451, dissolved in assay buffer at a concentration of 10 mg/mL), 1 mL of the tripeptide Met-Ala-Ser (Bachem) dissolved in assay buffer at concentration of 50 mM, 1 mL of ortho-dianisidine (Sigma Catalog No. D-1954, freshly made solution in water at a concentration of 10 mg/mL), and MetAP2 at a final concentration of 1.5 mg/mL was rapidly mixed and added to each cell containing test or control compound. The absorbence at 450 nanometers was measured every 20 seconds over a period of twenty minutes using an automatic plate reader (Molecular Devices, California, USA). The Vmax in mOD/min, calculated for each well, was used to represent MetAP2 activity. The $IC_{50}$ for each inhibitor was obtained by plotting the remaining activity versus inhibitor concentrations. Representative compounds of the present invention had $IC_{50}$'s between about 0.030 µM and about 1.80 µM. Preferred compounds of the present invention had $IC_{50}$'s between about 0.030 and about 0.05 µM.

As the literature has established a casual link between inhibition of MetAP2 and the resultant inhibition of endothelial cell proliferation and angiogenesis, it can be inferred that the compounds of the invention, including, but not limited to those specified in the examples, possess antiangiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder, and urothelium), female genital tract (including cervix, uterus, and ovaries as well as choriocarcinoma and gestational trophoblastic disease), male genital tract (including prostate, seminal vesicles, testes, and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. The compounds of the invention can also be useful in the treatment of the aforementioned conditions by mechanisms other than the inhibition of angiogenesis.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathologic consequence such as cat scratch disease (*Rochele minutesalia quintosa*) and ulcers (*Helicobacter pylori*). The compounds of the invention are also useful to reduce bleeding by administration prior to surgery, especially for the treatment of resectable tumors.

Synthetic Methods

Abbreviations which have been used in the descriptions of the scheme and the examples that follow are: BOC for tert-butoxycarbonyl; PCC for pyridinium chlorochromate; EDC for 1-(3-dimethylaminopropyl)-3-ethylcarbodiimide hydrochloride; HOAT for 1-hydroxy-7-azabenzotriazole; DCC for 1,3-dicyclohexylcarbodiimide; HOBT for 1-hydroxybenzotriazole; DMSO for dimethylsulfoxide; BOC-ON for [2-(tert-butoxycarbonyloxyimino)-2-phenylacetonitrile; and THF for tetrahydrofuran.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R^1$, and $R^2$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

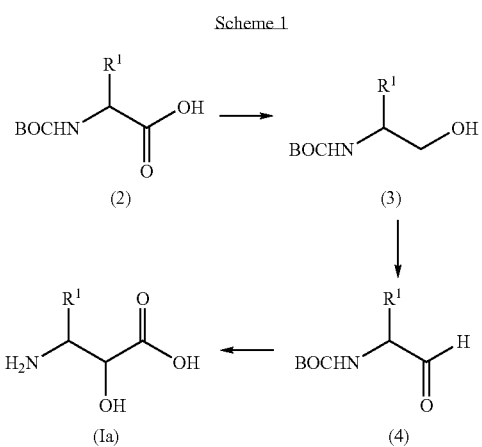

As shown in Scheme 1, compounds of formula (2) can be converted to compounds of formula (3) by treatment with a reducing agent. Examples of reducing agents include sodium bis(2-methoxyethoxy)aluminum hydride (Red-Al®), lithium aluminum hydride, and borane. Oxidation of compounds of formula (3) can be accomplished by treatment with an oxidizing agent such as sulfur trioxide pyridine complex, PCC, or the Dess-Martin periodinane to provide compounds of formula (4). Conversion of compounds of formula (2) to compounds of formula (4) may also be achieved by conversion to the N-methoxy-N-methylamide using N,O-dimethylhydroxylamine and an activating agent such as DCC or EDCI, followed by treatment with a reducing agent such as lithium aluminum hydride. Reacting compounds of formula (4) with trimethylsilylcyanide or sodium bisulfite and potassium cyanide provides the cyanohydrin which can be treated in situ with a strong acid such as HCl to simultaneously hydrolyze the cyano group and remove the protecting group, providing compounds of formula (Ia) (compounds of formula (I) where $R^2$ is hydrogen).

Scheme 2

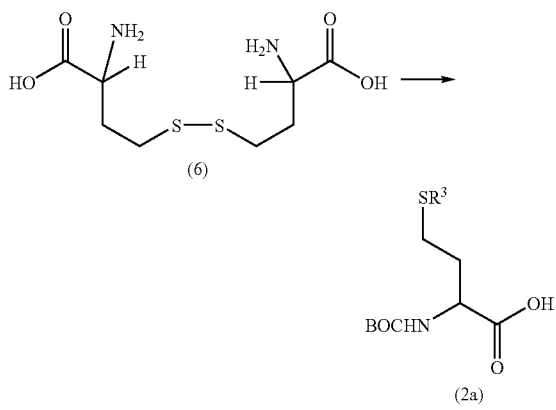

Compounds of formula (2a) can be prepared according to the procedure shown in Scheme 2. Reduction of compounds of formula (6) with liquid ammonia and sodium followed by treatment with an alkyl halide provides compounds of formula (2a) where $R^3$ is alkyl. Alternatively, compounds of formula (2a) can be prepared by treating compounds of formula (6) with liquid ammonia and sodium followed by a strong acid (such as HCl) and an appropriately substituted alcohol ($R^3OH$).

Scheme 3

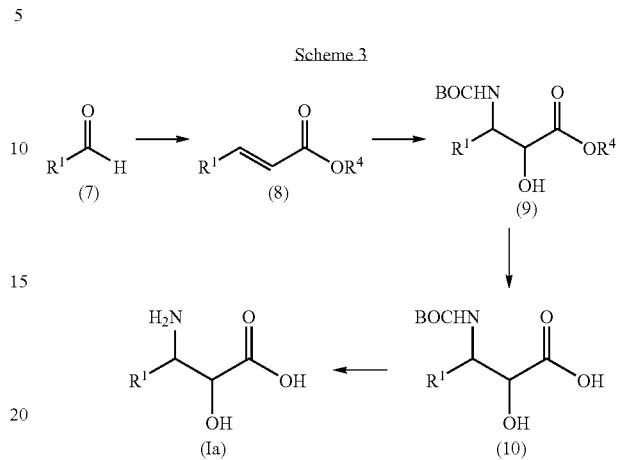

Scheme 3 shows the synthesis of compounds of formula (Ia). Compounds of formula (7) can be converted to compounds of formula (8) ($R^4$ is an alkyl group) by treatment with the appropriately substituted phosphonate in the presence of a base such as sodium hydride, potassium hydride, or lithium hexamethyldisilazide. Conversion of compounds of formula (8) to compounds of formula (9) can be accomplished by treatment with tert-butylcarbamate, tert-butylhypochlorite, and NaOH, followed by treatment with potassium osmate and either hydroquinine 1,4-phthalazinediyl diether or 1,4-phthalazinediyl diether (depending on which enantiomer is desired). Hydrolysis of the ester can be accomplished by methods known to those of ordinary skill in the art (for example, lithium hydroxide and hydrogen peroxide) to provide compounds of formula (10), which can be deprotected using conditions known to those of ordinary skill in the art (such as HCl) to provide compounds of formula (Ia).

Scheme 4

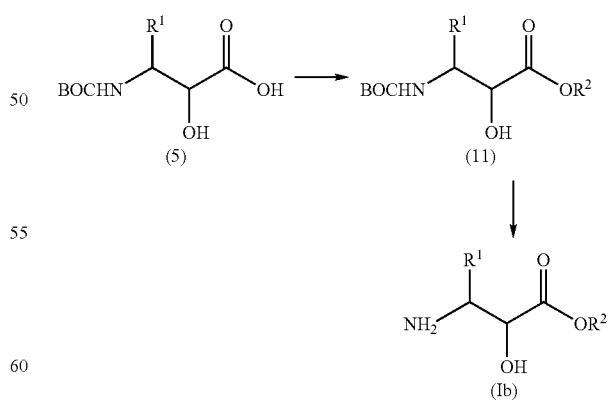

Compounds of formula (Ib) can be prepared by the methods shown in Scheme 4. Compounds of formula (5) can be esterified by treatment with an alkylating agent such as trimethylsilyldiazomethane or by coupling with the corre sponding alcohol (R²OH) in the presence of a coupling agent such as EDC and HOAT or DCC and HOBT to provide compounds of formula (11). Conversion of compounds of formula (11) to compounds of formula (Ib) (compounds of formula (I) where R² is other than hydrogen) can be accomplished by methods known to those of ordinary skill in the art (for example, treatment with HCl).

useful and readily understood description of its procedures and conceptual aspects.

Compounds of the invention were named by ACD/ChemSketch version 5.0 (developed by Advanced Chemistry Development, Inc., Toronto, ON, Canada) or were given names which appeared to be consistent with ACD nomenclature.

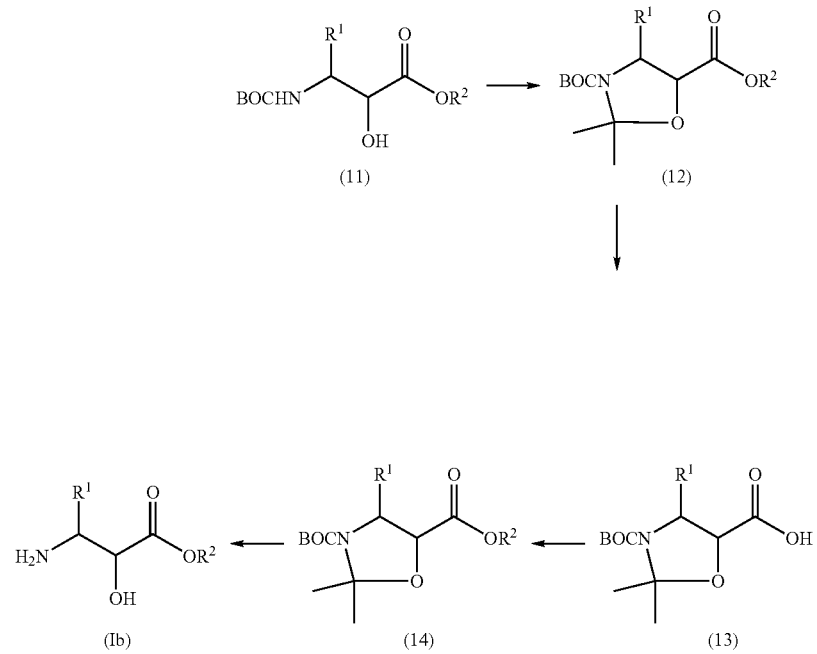

Compounds of formula (Ib) can also be prepared by the procedures described in Scheme 5. Compounds of formula (11) can be treated with 2,2-dimethoxypropane in the presence of an acid such as methylbenzenesulfonic acid or p-toluenesulfonic acid to provide compounds of formula (12). Hydrolysis of the ester using conditions known to those of ordinary skill in the art (for example, lithium hydroxide) provides compounds of formula (13). Esterification of compounds of formula (13) can be accomplished by treatment with an appropriately substituted alcohol (R²OH) and a coupling agent such as EDC and HOAT or DCC and HOBT. Compounds of formula (14) can be treated with a strong acid such as HCl in the presence of water to provide compounds of formula (Ib).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most

EXAMPLE 1

(2RS,3R)-3-amino-2-hydroxy-5-(methylsulfanyl) pentanoic acid

EXAMPLE 1A tert-butyl (1R)-1-(hydroxymethyl)-3-(methylsulfanyl)propylcarbamate

A solution of N-(tert-butoxycarbonyl)-D-methionine (12.47 g, 50 mmol) and sodium bis(2-methoxyethoxy)aluminum hydride (Red-Al®) (50 mmol) in dry toluene (125 mL) was stirred at 0° C. for 30 minutes, then at ambient temperature for 1 hour. The mixture was treated with aqueous Rochelle salt and extracted with diethyl ether. The extract was washed sequentially with brine and aqueous NaHCO₃, dried (MgSO₄), filtered, and concentrated to provide the desired product (9.05 g).

EXAMPLE 1B tert-butyl (1R)-1-formyl-3-(methylsulfanyl)propylcarbamate

A solution of Example 1A (9.05 g, 38.5 mmol), sulfur trioxide pyridine complex (30.64 g, 192.5 mmol), and triethylamine (26.8 mL, 192.5 mmol) in DMSO (30 mL)

was stirred at ambient temperature for 30 minutes, cooled to 0° C., treated sequentially with water (20 mL) and saturated aqueous KHSO$_4$ (120 mL), and extracted with ethyl acetate. The extract was washed sequentially with saturated aqueous KHSO$_4$ and brine, dried (MgSO$_4$), filtered, and concentrated to provide the desired product (9.00 g).

EXAMPLE 1C (2RS,3R)-3-amino-2-hydroxy-5-(methylsulfanyl) pentanoic acid

A solution of Example 1B (9.00 g, 38.5 mmol) and sodium bisulfite (3.80 g, 36.6 mmol) in water (200 mL) was stirred at 5° C. for 72 hours, warmed to ambient temperature, treated with a mixture of potassium cyanide (2.51 g, 38.6 mmol) in ethyl acetate (250 mL), and stirred for 4 hours. The separated ethyl acetate layer was washed sequentially with water and brine, dried (MgSO$_4$), filtered, and concentrated. The concentrate was dissolved in dioxane (75 mL) and 12M HCl (75 mL), heated to reflux for 16 hours, concentrated, dissolved in water (8 mL) and acetone (300 mL), adjusted to pH 5.5 with 1M NaOH, and filtered. The filter cake was dried under vacuum to provide the desired product (5.81 g). MS (ESI(+)Q1MS) m/e 180 (M+H)$^+$, 202 (M+Na)$^+$; MS (ESI(−)) m/e 178 (M−H)$^−$; $^1$H NMR (300 MHz, D$_2$O) δ 4.25 (d, 0.5H), 4.14 (d, 0.5H), 3.78 (m, 0.5H), 3.66 (m, 0.5H), 2.65 (m, 2H), 2.13 (s, 1.5H), 2.09 (s, 1.5H), 1.93 (m, 2H).

EXAMPLE 2

(2RS,3R)-3-amino-5-(ethylsulfanyl)-2-hydroxypentanoic acid

EXAMPLE 2A (2RS,3R)-3-[(tert-butoxycarbonyl)amino]-5-(ethylsulfanyl)-2-hydroxypentanoic acid The desired product was prepared by substituting (2R)-2-((tert-butoxycarbonyl)amino)-4-(ethylsulfanyl)butanoic acid for (2R)-2-((tert-butoxycarbonyl)amino)-3-cyclohexylpropanoic acid in Examples 3A–3C. MS (ESI) m/e 294 (M+H)$^+$.

EXAMPLE 2B (2RS,3R)-3-amino-5-(ethylsulfanyl)-2-hydroxypentanoic acid

The desired product was prepared by substituting Example 2A for Example 3C in Example 3D. MS (ESI) m/e 194 (M+H)$^+$; $^1$H NMR (300 MHz, DMSO-d$_6$) δ 8.14 (br s, 0.6H), 7.95 (br s, 1.4H), 4.35 (d, 0.3H), 4.16 (d, 0.7H), 3.70 (m, 0.3H), 3.46 (m, 0.7H), 2.63 (m, 2H), 2.49 (m, 2H), 1.84 (m, 2H), 1.18 (m, 3H).

EXAMPLE 3

(2RS,3R)-3-amino-4-cyclohexyl-2-hydroxybutanoic acid

EXAMPLE 3A tert-butyl (1R)-2-cyclohexyl-1-(hydroxymethyl)ethylcarbamate

A solution of (2R)-2-((tert-butoxycarbonyl)amino)-3-cyclohexylpropanoic acid (30.4 g, 112 mmol) in toluene (300 mL) at 0° C. was treated with sodium bis(2-methoxyethoxy) aluminum hydride (Red-Al®) (115 mmol) over 45 minutes. The mixture was stirred for 30 minutes, warmed to room temperature, stirred for 1 hour, treated with aqueous Rochelle salt, and extracted with diethyl ether. The extract was washed sequentially with brine and aqueous NaHCO$_3$, dried (MgSO$_4$), filtered, and concentrated to provide the desired product.

EXAMPLE 3B tert-butyl (1R)-2-cyclohexyl-1-formylethylcarbamate

A solution of Example 3A (25.8 g, 100 mmol), sulfur trioxide pyridine complex (79.6 g, 500 mmol), and triethylamine (69.7 mL, 500 mmol) in DMSO (70 mL) at room temperature was stirred for 30 minutes, cooled to 0° C., treated with water and saturated aqueous KHSO$_4$, and extracted with ethyl acetate. The extract was washed sequentially with saturated aqueous KHSO$_4$ and brine, dried (MgSO$_4$), filtered, and concentrated to provide the desired product.

EXAMPLE 3C (2RS,3R)-3-[(tert-butoxycarbonyl)amino]-4-cyclohexyl-2-hydroxybutanoic acid A solution of Example 3B (19.7 g, 77.1 mmol) and sodium bisulfite (8.0 g, 77.1 mmol) in water (500 mL) at 5° C. was stirred for 24 hours, warmed to room temperature, treated with a solution of potassium cyanide (5.1 g, 78.8 mmol) in ethyl acetate (350 mL), and stirred for 5 hours. The aqueous phase was separated and extracted with ethyl acetate. The combined extracts were washed sequentially with water and brine, dried (MgSO$_4$), filtered, and concentrated. The concentrate was dissolved in dioxane (150 mL), treated with 12M HCl (150 mL), heated to reflux, stirred for 21 hours, and cooled to room temperature. The mixture was concentrated, dissolved in a mixture of water (30 mL) and acetone (200 mL), adjusted to pH 5.5 with 1M NaOH, treated with acetone (3.5 L), and cooled to 0° C. for 4 hours. The resulting precipitate was collected by filtration. The filter cake was dried, dissolved in 1:1 water/dioxane, treated with BOC-ON (1.2 eq.), and triethylamine (2 eq.), heated to 45° C., stirred for 15 hours, treated with 10% aqueous KHSO$_4$, and extracted with ethyl acetate. The extract was washed sequentially with water and brine, dried (MgSO$_4$), filtered, and concentrated to provide the desired product.

EXAMPLE 3D (2RS,3R)-3-amino-4-cyclohexyl-2-hydroxybutanoic acid

A solution of Example 3C (75 mg, 0.25 mmol) in 4M HCl in dioxane (2 mL) at room temperature was stirred for 1 hour, concentrated, then purified by reverse phase HPLC with acetonitrile/water to provide the desired product. MS (ESI) m/e 202 (M+H)$^+$; $^1$H NMR (300 MHz, DMSO-d$_6$) δ 7.81 (br s, 2H), 4.07 (d, 1H), 3.35 (m, 1H), 1.80–1.67 (m, 5H), 1.57–1.51 (m, 1H), 1.46–1.17 (m, 5H), 1.00–0.90 (m, 2H); Anal. Calcd. for C$_{10}$H$_{20}$ClNO$_3$: C, 50.52; H, 8.48; N, 5.89. Found: C, 50.18; H, 8.56; N, 5.67.

EXAMPLE 5

(2RS,3R)-3-amino-3-cyclohexyl-2-hydroxypropanoic acid

The desired product was prepared by substituting (2R)-2-((tert-butoxycarbonyl)amino)-2-(cyclohexyl)ethanoic acid for (2R)-2-((tert-butoxycarbonyl)amino)-3-cyclohexylpropanoic acid in Examples 3A–3D. MS (ESI) m/e 188 (M+H)$^+$; $^1$H NMR (300 MHz, DMSO-d$_6$) δ 7.92 (br s, 0.6H), 7.77 (br s, 1.4H), 4.31 (d, 0.3H), 4.12 (d, 0.7H), 3.69 (m, 0.7H), 3.48 (m, 0.3H), 1.85–1.70 (m, 4H), 1.70–1.51 (m, 2H), 1.46–1.17 (m, 3H), 1.00–0.90 (m, 2H).

EXAMPLE 6

(2RS,3R)-3-amino-2-hydroxy-5-phenylpentanoic acid

EXAMPLE 6A (2RS,3R)-3-[(tert-butoxycarbonyl)amino]-2-hydroxy-5-phenylpentanoic acid The desired product was prepared by substituting (2R)-2-((tert-butoxycarbonyl)amino)-4-(phenyl)butanoic acid for (2R)-2-((tert-butoxycarbonyl)amino)-3-cyclohexylpropanoic acid in Examples 3A–3C. MS (ESI) m/e 310 (M+H)$^+$.

EXAMPLE 6B (2RS,3R)-3-amino-2-hydroxy-5-phenylpentanoic acid

The desired compound was obtained by substituting Example 6A for Example 3C in Example 3D. MS (ESI(+)) m/e 210 (M+H)$^+$; $^1$H NMR (300 MHz, DMSO-d$_6$) δ 7.34–7.16 (m, 5H), 4.19 (br d, 1H), 2.76–2.65 (m, 2H), 1.97–1.68 (m, 2H).

EXAMPLE 7

(2RS,3R)-3-amino-2-hydroxy-5-(isopropylsulfanyl) pentanoic acid

EXAMPLE 7A (2R)-2-[(tert-butoxycarbonyl)amino]-4-(isopropylsulfanyl)butanoic acid A solution of D-homocystine (20 g, 75 mmol) in liquid ammonia (600 mL) was treated sequentially with sodium (8.9 g, 390 mmol) and 2-bromopropane (20 mL, 210 mmol). The ammonia was allowed to evaporate under a stream of nitrogen, and the residue was dissolved in 1:1 2-propanol/water (500 mL), treated with di-tert-butyl dicarbonate (50 g, 230 mmol), stirred at room temperature for 6 hours, then concentrated. The residue was dissolved in water and the pH was adjusted to 10 with 50% NaOH. The solution was washed twice with diethyl ether, adjusted to pH 2 with 12M HCl, and extracted twice with ethyl acetate. The extracts were dried (MgSO$_4$), filtered, then concentrated to provide the desired product. MS (ESI) m/e 279 (M+H)$^+$.

EXAMPLE 7B (2RS,3R)-3-[(tert-butoxycarbonyl)amino]-2-hydroxy-5-(isopropylsulfanyl)pentanoic acid The desired product was prepared by substituting Example 7A for (2R)-2-((tert-butoxycarbonyl)amino)-3-cyclohexylpropanoic acid in Examples 3A–3C. MS (ESI(+)) m/e 308 (M+H)$^+$.

EXAMPLE 7C (2RS,3R)-3-amino-2-hydroxy-5-(isopropylsulfanyl) pentanoic acid

The desired product was prepared by substituting Example 7B for Example 3C in Example 3D. MS (ESI) m/e 208 (M+H)$^+$; $^1$H NMR (300 MHz, DMSO-d$_6$) δ 7.34 (br s, 0.6H), 7.20 (br s, 1.4H), 4.10 (d, 0.3H), 4.02 (d, 0.7H), 3.70 (m, 0.7H), 3.46 (m, 0.3H), 2.92 (m, 1H), 2.61 (m, 2H), 1.83–1.75 (m, 2H), 1.21 (d, 2.1H), 1.19 (d, 0.9H).

EXAMPLE 8

(2S,3R,4S)-3-amino-2-hydroxy-4-(3-hydroxypropyl)-7-methyloctanoic acid

EXAMPLE 8A 5-methylhexanoyl chloride

A mixture of 5-methylhexanoic acid (25 mL, 175 mmol) and thionyl chloride (50 mL, 0.69 mol) was stirred at reflux for 90 minutes. The mixture was concentrated, then distilled at reduced pressure to give the desired product (22.35 g).

EXAMPLE 8B (4R)-4-benzyl-3-(5-methylhexanoyl)-1,3-oxazolidin-2-one

To a −78° C. solution of 4(R)-benzyl-2-oxazolidinone (21.28 g, 0.12 mol) in THF (360 mL) was added n-butyllithium (48 mL, 2.5M in hexane, 120 mmol). After 10 minutes Example 8A (19.76 g, 0.134 mol) was added. After 30 minutes the mixture was warmed to 0° C., and quenched with saturated ammonium chloride. The supernatant was decanted and concentrated. The residue was partitioned between water and ethyl acetate and the organic layer was washed sequentially with water, 1M sodium bicarbonate, water, and brine, dried (MgSO$_4$), filtered, and concentrated to provide the desired product. MS (ESI) m/e 290 (M+H)$^+$.

EXAMPLE 8C (4R)-4-benzyl-3-[(2S)-2-(3-methylbutyl)-4-pentenoyl]-1,3-oxazolidin-2-one To a stirred −78° C. solution of Example 8B (15.65 g, 54.2 mmol) in THF (160 mL) was added sodium bis(trimethylsilyl)amide (55 mL, 1M in THF). The reaction mixture was stirred for 45 minutes and allyl bromide (5.3 mL, 60.9 mmol) was added. The reaction mixture was stirred for 90 minutes, warmed to 0° C., and stirred an additional 90 minutes. The reaction was quenched with saturated ammonium chloride, concentrated, and partitioned between water and ethyl acetate. The organic layer was washed sequentially with water, 1M sodium bicarbonate, water, and brine, dried ($MgSO_4$), filtered, and concentrated to provide the desired product. MS (ESI) m/e 330 (M+H)$^+$.

EXAMPLE 8D (2S)-2-(3-methylbutyl)-4-pentenoic acid

To a 0° C. solution of Example 8C (17.3 g, 52.6 mmol) in THF (200 mL) was added water (25 mL) and 30% hydrogen peroxide (25 mL, 220 mmol). A solution of lithium hydroxide monohydrate (4.38 g, 104 mmol) in water (100 mL) was added and the resulting solution was stirred for 12 hours. The mixture was quenched with aqueous $NaHSO_3$ then concentrated and made basic with 5M NaOH. The aqueous phase was washed with ethyl acetate, then acidified with concentrated HCl to pH 3 and extracted twice with ethyl acetate. The combined extracts were dried ($MgSO_4$), filtered, and concentrated to provide the desired product. MS (ESI(+)) m/e 171 (M+H)$^+$.

EXAMPLE 8E (2S)-N-methoxy-N-methyl-2-(3-methylbutyl)-4-pentenamide

A solution of Example 8D (4.54 g, 26.7 mmol), N,O-dimethyl hydroxylamine hydrochloride (5.6 g, 57 mmol), 1-(3-dimethylaminopropyl)-3-ethylcarbodiimide hydrochloride (5.19 g, 27 mmol), 1-hydroxybenzotriazole (4.12 g, 30.5 mmol), and N-methylmorpholine (7.0 mL, 64 mmol) in dichloromethane (270 mL) at room temperature was stirred for 4 hours, diluted with dichloromethane, washed sequentially with aqueous $NaHCO_3$, brine, 10% $KHSO_4$, and brine, dried ($MgSO_4$), filtered, and concentrated. Flash column chromatography (silica gel, 10% ethyl acetate/hexanes) provided the desired product. MS (ESI(+)) m/e 214 (M+H)$^+$.

EXAMPLE 8F (2S)-2-(3-hydroxypropyl)-N-methoxy-N,5-dimethylhexanamide

A solution of Example 8E (2.31 g, 10.8 mmol), and THF-borane complex (12.0 mL, 1.0M in THF) in THF (10 mL) at 0° C. was stirred for 2.5 hours, treated with 30% aqueous hydrogen peroxide (10 mL, 88 mmol) and pH 7 buffer solution (20 mL), stirred vigorously for 90 minutes, diluted with dichloromethane, washed with pH 7 buffer, dried ($Na_2SO_4$), filtered, and concentrated to provide the desired product. MS (ESI) m/e 232 (M+H)$^+$.

EXAMPLE 8G (2S)-2-(3-{[tert-butyl(dimethyl)silyl]oxy}propyl)-N-methoxy-N,5-dimethylhexanamide A solution of Example 8F (2.58 g, 11.1 mmol), tert-butyldimethylsilyl trifluoromethanesulfonate (2.8 mL, 12 mmol), and 2,6-lutidine (1.5 mL, 13 mmol) in dichloromethane (100 mL) at 0° C. was stirred for 2 hours, diluted with dichloromethane, washed sequentially with 10% $KHSO_4$, aqueous $NaHCO_3$, and brine, dried ($MgSO_4$), filtered, and concentrated to provide the desired product. MS (ESI) m/e 346 (M+H)$^+$.

EXAMPLE 8H (2S)-2-(3-{[tert-butyl(dimethyl)silyl]oxy}propyl)-5-methylhexanal

A solution of Example 8F (3.16 g, 9.16 mmol) and lithium aluminum hydride (0.34 g, 9.2 mmol) in diethyl ether (100 mL) at room temperature was stirred 30 minutes, treated with 1M $NaHSO_4$, diluted with di ethyl ether, washed sequentially with 10% $NaHSO_4$, and brine, dried ($MgSO_4$), filtered, and concentrated to provide the desired product. MS (ESI) m/e 287 (M+H)$^+$.

EXAMPLE 8I benzyl (2E,4S)-4-(3-{[tert-butyl(dimethyl)silyl]oxy}propyl)-7-methyl-2-octenoate A solution of Example 8H (2.61 g, 9.16 mmol), benzyl diethylphosphonoacetate (2.83 g, 9.90 mmol), and sodium hydride (0.24 g, 10 mmol) in benzene (40 mL) at room temperature was stirred 2 hours, diluted with ethyl acetate, washed sequentially with saturated aqueous $NH_4Cl$ and pH 7 buffer, dried ($MgSO_4$), filtered, and concentrated. Flash column chromatography (silica gel, 2:1 hexanes/$CH_2Cl_2$) provided the desired product. MS (ESI) m/e 419 (M+H)$^+$.

EXAMPLE 8J benzyl (2S,3R,4S)-3-[(tert-butoxycarbonyl)amino]-4-(3-1{[tert-butyl(dimethyl)silyl]oxy}propyl)-2-hydroxy-7-methyloctanoate The desired product was prepared by substituting Example 8I for Example 9B in Example 9C. Flash column chromatography (silica gel, 10% ethyl acetate/hexanes) provided the purified product. MS (ESI) m/e 552 (M+H)$^+$.

EXAMPLE 8K (2S,3R,4S)-3-amino-2-hydroxy-4-(3-hydroxypropyl)-7-methyloctanoic acid A mixture of Example 8J (115 mg, 0.027 mmol) and 10% Pd/C in THF (5 mL) under a hydrogen atmosphere at room temperature was stirred for 3.5 hours and filtered. The filtrate was treated with tetrabutylammonium fluoride (0.25 mL, 1.0M in THF) for 18 hours, diluted with diethyl ether, washed twice with 1M HCl, dried ($Na_2SO_4$), filtered, and concentrated. The concentrate was dissolved in 4M HCl in dioxane (2 mL), stirred for 1 hour, and concentrated to provide the desired product. MS (ESI) m/e 248 (M+H)$^+$; $^1$H NMR (300 MHz, DMSO-$d_6$) δ 4.21 (d, 1H), 3.73 (m, 1H), 3.67 (m, 1H), 3.56 (m, 1H), 1.60–1.48 (m, 4H), 1.43–1.37 (m, 2H), 1.35–1.23 (m, 4H), 0.91 (d, 6H).

EXAMPLE 9

(2S,3R)-3-amino-2-hydroxy-6-phenylhexanoic acid

EXAMPLE 9A 4-phenylbutanal

A solution of 4-phenylbutyric acid (1.64 g, 10.0 mmol), N,O-dimethyl hydroxylamine hydrochloride (1.58 g, 16 mmol), 1-(3-dimethylaminopropyl)-3-ethylcarbodiimide hydrochloride (2.06 g, 10.7 mmol), 1-hydroxybenzotriazole (1.56 g, 11.6 mmol), and N-methylmorpholine (2.8 mL, 26 mmol) in dichloromethane (40 mL) at room temperature was stirred for 16 hours, diluted with dichloromethane, washed sequentially with aqueous NaHCO$_3$, brine, 10% KHSO$_4$, and brine, dried (MgSO$_4$), filtered, and concentrated. A mixture of the concentrate and lithium aluminum hydride (9.0 mmol, 1 equiv.) in diethyl ether (49 mL) at room temperature was stirred for 90 minutes, treated with 1M NaHSO$_4$, diluted with diethyl ether, washed sequentially with 10% KHSO$_4$, and brine, dried (MgSO$_4$), filtered, and concentrated to provide the desired product. MS (ESI) m/e 148 (M+H)$^+$.

EXAMPLE 9B ethyl (2E)-6-phenyl-2-hexenoate

A solution of Example 9A (1.17 g, 7.9 mmol), triethyl phosphonoacetate (1.05 mL, 7.9 mmol), lithium bromide (0.70 g, 8.1 mmol), and triethylamine (1.1 mL, 7.8 mmol) in THF (80 mL) at room temperature was stirred for 16 hours, quenched with water, stirred for 15 minutes, diluted with ethyl acetate, washed sequentially with pH 7 buffer and brine, dried (MgSO$_4$), filtered, and concentrated. The concentrate was purified by flash column chromatography on silica gel with 1:1/dichloromethane:hexanes to provide the desired product. MS (ESI) m/e 218 (M+H)$^+$.

EXAMPLE 9C ethyl (2S,3R)-3-[(tert-butoxycarbonyl)amino]-2-hydroxy-6-phenylhexanoate A solution of tert-butylcarbamate (1.00 g, 8.55 mmol), tert-butylhypochlorite (0.96 mL, 8.5 mmol), and 0.5M NaOH (17 mL, 8.5 mmol) in 1-propanol (30 mL) at room temperature was stirred for 15 minutes. Example 9B (0.614 g, 2.82 mmol), potassium osmate dihydrate (0.030 g, 0.08 mmol) and hydroquinine 1,4-phthalazinediyl diether (0.109 g, 0.14 mmol) were added, and the mixture was stirred at 0° C. for 2 hours, diluted with ethyl acetate, washed sequentially with water, 1M HCl, aqueous NaHCO$_3$, and brine, dried (MgSO$_4$), filtered, and concentrated. The concentrate was purified by flash column chromatography on silica gel with 1:4/ethyl acetate:hexanes to provide the desired product. MS (ESI) m/e 352 (M+H)$^+$.

EXAMPLE 9D (2S,3R)-3-[(tert-butoxycarbonyl)amino]-2-hydroxy-6-phenylhexanoic acid A solution of Example 9C (0.316 g, 0.90 mmol), 30% hydrogen peroxide (0.40 mL, 3.5 mmol), and lithium hydroxide monohydrate (0.076 g, 1.8 mmol) in 3:1 tetrahydrofuran/water (8 mL) was stirred at 0° C. for 3 hours and concentrated. The concentrate was dissolved in water and the pH adjusted to 10 with 1M NaOH. The solution was washed twice with diethyl ether, adjusted to pH 2 with 1M HCl, and extracted twice with ethyl acetate. The combined extracts were dried (MgSO$_4$), filtered, and concentrated to provide the desired product. MS (ESI) m/e 324 (M+H)$^+$.

EXAMPLE 9E (2S,3R)-3-amino-2-hydroxy-6-phenylhexanoic acid

A solution of Example 9D (25.7 mg, 0.08 mmol) in 4M HCl in dioxane (2 mL) was stirred at room temperature for 1 hour and concentrated to provide the desired product. MS (ESI) m/e 224 (M+H)$^+$; $^1$H NMR (300 MHz, DMSO-d$_6$) δ 7.29 (m, 2H), 7.18 (m, 3H), 4.11 (d, 1H), 3.69 (m, 1H), 2.57 (m, 2H), 1.73–1.49 (m, 4H).

EXAMPLE 10

(2RS,3R)-3-amino-5-(tert-butylsulfanyl)-2-hydroxypentanoic acid

EXAMPLE 10A (2R)-2-[(tert-butoxycarbonyl)amino]-4-(tert-butylsulfanyl)butanoic acid A solution of D-homocystine (3.0 g, 11 mmol) in liquid ammonia (100 mL) was treated with sodium (1.3 g, 56 mmol). The ammonia was allowed to evaporate under a stream of nitrogen, and the residue was dissolved in 1M HCl (10 mL). The pH was adjusted to 0 with concentrated HCl, treated with tert-butanol (5 mL, 53 mmol), heated to reflux for 16 hours, and concentrated. The concentrate was dissolved in 1:1 2-propanol/water (80 mL), treated with di-tert-butyl dicarbonate (20.2 g, 92.7 mmol), stirred at room temperature for 16 hours, and concentrated. The concentrate was dissolved in water adjusted to pH 10 with 50% NaOH. The solution was washed twice with diethyl ether, adjusted to pH 2 with HCl, and extracted twice with ethyl acetate. The combined extracts were dried (MgSO$_4$), filtered, then concentrated to provide the desired product. MS (ESI) m/e 292 (M+H)$^+$.

EXAMPLE 10B (2RS,3R)-3-amino-5-(tert-butylsulfanyl)-2-hydroxypentanoic acid

The desired product was prepared by substituting Example 10A for (2R)-2-((tert-butoxycarbonyl)amino)-3-cyclohexylpropanoic acid in Examples 3A–3D. MS (ESI) m/e 222 (M+H)$^+$; $^1$H NMR (300 MHz, DMSO-d$_6$) δ 4.38 (d, 0.5H), 4.28 (d, 5H), 3.73–3.66 (m, 1H), 2.72–2.63 (m, 2H), 1.95–1.84 (m, 2H), 1.34 (s, 4.5H), 1.32 (s, 2.5H).

EXAMPLE 11 methyl (3R)-3-amino-2-hydroxy-5-(methylsulfanyl)pentanoate

EXAMPLE 11A (3R)-3-[(tert-butoxycarbonyl)amino]-2-hydroxy-5-(methylsulfanyl)pentanoic acid A solution of Example 1C (2.68 g, 12.5 mmol), triethylamine (3.47 ml, 75.0 mmol), and 2-(tert-butyoxycarbonyloxyimino)-2-phenylacetonitrile (3.22 g, 13.0 mmol) in 30% aqueous dioxane was heated to 50° C. for 6 hours, cooled to ambient temperature, and concentrated. The residue was diluted with aqueous sodium hydroxide (0.25M, 50 mL) and extracted twice with ethyl acetate. The aqueous layer was acidified to pH 3 with 1M $H_3PO_4$ and extracted five times with chloroform. The combined extracts were washed with brine, dried ($MgSO_4$), filtered, and concentrated to provide the desired product (1.62 g). MS (ESI) m/e 278 (M–H)⁻.

EXAMPLE 11B (3R)-3-[(tert-butoxycarbonyl)amino]-5-(methylsulfanyl)-2-(tetrahydro-2H-pyran-2-yloxy)pentanoic acid A solution of Example 11A (1.62 g, 5.8 mmol), 3,4-dihydro-2H-pyran (0.64 mL, 70 mmol), and pyridinium p-toluenesulfonate (0.15 mL, 0.60 mmol) in dichloromethane (30 mL) was heated to 35° C. for 16 hours and concentrated. The concentrate was diluted with aqueous sodium hydroxide (0.25M, 15 mL) and extracted twice with ethyl acetate. The aqueous layer was adjusted to pH 3 with aqueous $H_3PO_4$ (1.0M) and extracted three times with ethyl acetate. These three extracts were combined, washed sequentially with water (20 mL) and brine (20 mL), dried ($MgSO_4$), filtered, and concentrated to provide the desired product (0.61 g). MS (APCI(+)) m/e 364 (M+H)⁺.

EXAMPLE 11C methyl (3R)-3-((tert-butoxycarbonyl)amino)-2-hydroxy-5-(methylthio)pentanoate A solution of Example 11B (0.25g, 0.68 mmol) and trimethylsilyldiazomethane (2.0M in hexanes, 15 mL) in THF at room temperature was stirred for 4 hours, treated with acetic acid (1 mL), and concentrated. The residue was dissolved in methanol, treated with p-toluenesulfonic acid (10 mg), and heated to 55° C. for 16 hours. The mixture was concentrated and purified by flash column chromatography on silica gel with 25% ethyl acetate/hexanes to provide the desired product. MS (APCI(+)) m/e 294 (M+H)⁺.

EXAMPLE 11D methyl (3R)-3-amino-2-hydroxy-5-(methylsulfanyl)pentanoate

A solution of Example 11C in 4M HCl in dioxane (10 mL) at room temperature was stirred for 4 hours and concentrated to provide the desired product. MS (APCI(+)) m/e 194 (M–H)⁻; ¹H NMR (300 MHz, DMSO-$d_6$) δ 8.09 (br s, 2H), 7.94 (br s, 1H), 6.58 (m, 0.5H), 6.42 (m, 0.5H), 4.48 (m, 0.5H), 4.30 (m, 0.5H), 3.72 (s, 3H), 2.58 (m, 2H), 2.04 (s, 1.5H), 2.02 (s, 1.5H), 1.82 (m, 2H).

EXAMPLE 12 methyl (2RS,3R)-3-amino-4-cyclohexyl-2-hydroxybutanoate

EXAMPLE 12A methyl (2RS,3R)-3-(tert-butoxycarbonyl)amino-4-cyclohexyl-2-hydroxybutanoate A solution of Example 3C (10.234 g, 34 mmol), and trimethylsilyldiazomethane (2.0M in hexanes, 25 mL) in 3.5:1 benzene/methanol (232 mL) at room temperature was stirred at 0° C. for 1 hour, warmed to ambient temperature, stirred for 1 hour, quenched by the dropwise addition of acetic acid, concentrated to provide the desired product. MS (ESI) m/e 316 (M+H)⁺.

EXAMPLE 12B methyl (2RS,3R)-3-amino-4-cyclohexyl-2-hydroxybutanoate

The desired product was prepared by substituting Example 12A for Example 3C in Example 3D. MS (ESI) m/e 216 (M+H)⁺; ¹H NMR (300 MHz, $CD_3OD$) δ 4.42 (d, 0.3H), 4.22 (d, 0.7H), 3.80 (s, 2.1H), 3.77 (s, 0.9H), 3.14 (m, 1H), 1.80–1.67 (m, 5H), 1.57–1.51 (m, 1H), 1.46–1.17 (m, 5H), 1.00–0.90 (m, 2H).

EXAMPLE 13

(1S,2R)-2-amino-2,3-dihydro-1H-inden-1-yl (2RS,3R)-3-amino-4-cyclohexyl-2-hydroxybutanoate A solution of Example 3C (0.10 g, 0.33 mmol), (1S,2R)-1-amino-2-hydroxyindane (0.086 g, 0.58 mmol), 1-(3-dimethylaminopropyl)-3-ethylcarbodiimide hydrochloride (0.080 g, 0.41 mmol), 1-hydroxybenzotriazole (0.061 g, 0.45 mmol), and N-methylmorpholine (0.05 mL, 0.46 mmol) in 3:1 dichloromethane/DMF (4 mL) at room temperature was stirred for 16 hours, diluted with dichloromethane, washed sequentially with aqueous $NaHCO_3$, brine, 10% $KHSO_4$, and brine, dried ($MgSO_4$), filtered, and concentrated. The residue was dissolved in 4M HCl in dioxane (3 mL), stirred for 1 hour, concentrated, then purified by reverse phase HPLC with acetonitrile/water to provide the desired product. MS (ESI) m/e 333 (M+H)⁺; ¹H NMR (300 MHz, DMSO-$d_6$) δ 7.81 (br s, 2H), 7.40–7.17 (m, 4H), 6.65 (d, 1H), 5.52 (m, 1H), 4.18 (d, 1H), 3.14 (m, 1H), 2.55–2.45 (m, 2H), 1.80–1.67 (m, 5H), 1.57–1.51 (m, 1H), 1.46–1.17 (m, 5H), 1.00–0.90 (m, 2H).

EXAMPLE 14 benzyl (2S,3R)-3-amino-3-cyclopentyl-2-hydroxypropanoate

EXAMPLE 14A benzyl (2E)-3-cyclopentylacrylate

A solution of cyclopentanecaboxaldehyde (0.069 g, 0.70 mmol), benzyl (diethylethyl phosphono)acetate (0.100 g, 0.35 mmol), lithium bromide (0.030 g, 0.35 mmol), and triethylamine (0.049 mL, 0.35 mmol) in THF (1 mL) at room temperature was stirred for 16 hours, quenched with water, stirred for 15 minutes, diluted with ethyl acetate, washed sequentially with pH 7 buffer and brine, dried (MgSO$_4$), filtered, and concentrated to provide the desired product. MS (ESI) m/e 231 (M+H)$^+$.

EXAMPLE 14B benzyl (2S,3R)-3-[(tert-butoxycarbonyl)amino]-3-cyclopentyl-2-hydroxypropanoate The desired product was prepared by substituting Example 14A for Example 9B in Example 9C. MS (ESI) m/e 364 (M+H)$^+$.

EXAMPLE 14C benzyl (2S,3R)-3-amino-3-cyclopentyl-2-hydroxypropanoate

The desired product was prepared by substituting Example 14B for Example 3C in Example 3D. MS (ESI) m/e 264 (M+H)$^+$; $^1$H NMR (300 MHz, CD$_3$OD) δ 7.39 (m, 5H), 5.29 (dd, 2H), 4.04 (d, 1H), 3.88 (dd, 1H), 3.66 (s, 1H), 1.96 (m, 1H), 1.86 (m, 1H), 1.68 (m, 2H), 1.58 (m, 2H), 1.43 (m, 1H), 1.23 (m, 1H).

EXAMPLE 15 benzyl (2S,3R)-3-amino-3-cycloheptyl-2-hydroxypropanoate

The desired product was prepared by substituting cycloheptanecarboxaldehyde for cyclopentanecarboxaldehyde in Examples 14A–C. MS (ESI) m/e 292 (M+H)$^+$; $^1$H NMR (300 MHz, CD$_3$OD) δ 7.39 (m, 5H), 5.29 (dd, 2H), 4.09 (d, 1H), 3.78 (dd, 1H), 3.66 (s, 1H), 1.84 (m, 1H), 1.65 (m, 2H), 1.57 (m, 2H), 1.52 (m, 2H), 1.46 (m, 2H), 1.41 (m, 2H), 1.41 (m, 2H), 1.33 (m, 2H).

EXAMPLE 16

(2S)-2-(methylamino)-2-(1-naphthyl)ethyl (2S,3R)-3-amino-5-(ethylsulfanyl)-2-hydroxypentanoate

EXAMPLE 16A tert-butyl (1R)-2-hydroxy-1-(1-naphthyl)ethyl(methyl)carbamate and tert-butyl (1RS)-2-hydroxy-1-methyl-1-(1-naphthyl)ethyl(methyl)carbamate A mixture of sodium hydride (dispersion in 60% mineral oil, 440 mg, 10.9 mmol) and methyl (2R)-[(tert-butoxycarbonyl)amino](1-naphthyl)acetate (1.43 g, 4.54 mmol) in THF (20 mL) was stirred at 0° C. for 15 minutes, treated with methyl iodide (1.978 mL, 31.8 mmol), stirred at 0° C. for 2 hours, warmed to room temperature, and stirred for 16 hours. The mixture was diluted with ethyl acetate, washed sequentially with 10% aqueous KHSO$_4$ and brine, dried (MgSO$_4$), filtered, and concentrated to provide a mixture of mono- and di-methylated product (ratio: 4:1). The mixture (2.0 g) was dissolved in THF (20 mL), cooled to 0° C., treated with sodium bis(2-methoxyethoxy)aluminum hydride (Red-Al®) (6 mL), stirred for 1 hour, warmed to room temperature, stirred for 1 hour, quenched with aqueous Na$_2$SO$_4$ (10 mL), and extracted three times with ethyl acetate. The combined extracts were washed twice with brine, twice with 10% KHSO$_4$, once more with brine, twice with 10% sodium hydrogen carbonate, three additional times with brine, dried (MgSO$_4$), filtered, and concentrated. The concentrate was purified by flash column chromatography on silica gel with 10% ethyl acetate/hexanes to provide the desired products MS(ESI(+)) m/e 302 (M+H)$^+$ and 316 (M+H)$^+$.

EXAMPLE 16B (2R)-2-(methylamino)-2-(1-naphthyl)ethyl (2S,3R)-3-amino-5-(ethylsulfanyl)-2-hydroxypentanoate The desired product was prepared by substituting tert-butyl (1R)-2-hydroxy-1-(1-naphthyl)ethyl(methyl)carbamate from Example 16A and Example 2A for (1S,2R)-1-amino-2-hydroxyindane and Example 3C, respectively, in Example 13. The crude product was purified by reverse phase HPLC with acetonitrile/water to provide the desired product. MS (ESI(+)) m/e 377 (M+H)$^+$; $^1$H-NMR (300 MHz, DMSO-d$_6$) δ 8.29–8.19 (m, 1H), 8.06–8.00 (m, 3H), 7.71–7.58 (m, 3H), 6.48 (d, 1H), 5.60 (br s, 1H), 4.75–4.66 (m, 1H), 4.60–4.53 (m, 2H), 3.72–3.56 (m, 1H), 2.60 (br s, 3H), 2.48–2.26 (m, 3H, includes 2.33 (q)), 1.77–1.44 (m, 2H), 1.05 (t, 3H).

EXAMPLE 17

(2R)-2-(methylamino)-2-(1-naphthyl)ethyl (2S,3R)-3-amino-5-(ethylsulfanyl)-2-hydroxypentanoate The desired compound was obtained by substituting methyl (2S)-[(tert-butoxycarbonyl)amino](1-naphthyl)acetate for methyl (2R)-[(tert-butoxycarbonyl)amino](1-naphthyl)acetate in Examples 16A–B. MS (ESI(+)) m/e 377 (M+H)$^+$; $^1$H-NMR (300 MHz, DMSO-d$_6$) δ 8.32–8.25 (m, 1H), 8.08–7.99 (m, 3H), 7.72–7.54 (m, 3H), 6.63 (d, 1H), 5.62 (br s, 1H), 4.71–4.55 (m, 2H), 4.45–4.40 (m, 1H), 3.73–3.64 (m, 1H), 2.62 (br s, 3H), 2.53–2.42 (m, 3H, overlapped with solvent peaks), 1.94–1.70 (m, 2H), 1.17 (t, 3H).

EXAMPLE 18

2-(methylamino)-2-(1-naphthyl)propyl (3R)-3-amino-5-(ethylsulfanyl)-2-hydroxypentanoate The desired product was prepared by substituting tert-butyl (1RS)-2-hydroxy-1-methyl-1-(1-naphthyl)ethyl(methyl)carbamate from Example 16A and Example 2A for (1S,2R)-1-amino-2-hydroxyindane and Example 3C, respectively, in Example 13. MS (ESI(+)) m/e 391 (M+H)$^+$; $^1$H-NMR (300 MHz, DMSO-d$_6$) δ 8.15–8.03 (br s, 3H), 7.93–7.82 (br s, 3H), 7.66–7.56 (br s, 1H), 6.54 (d, 0.7H), 6.45 (d, 0.3H), 4.25–4.17 (br s, 0.3H), 4.13–4.05 (br s, 0.7H), 3.54–3.40 (m, 1H), 2.60 (br s, 3H), 2.67–2.43 (m, includes solvent peaks), 1.93–1.59 (m, 2H), 1.21–1.07 (m, 6H).

EXAMPLE 19

(2R)-2-(methylamino)-2-(1-naphthyl)ethyl (2S,3R)-3-amino-4-cyclohexyl-2-hydroxybutanoate The desired product was prepared by substituting tert-butyl (1R)-2-hydroxy-1-(1-naphthyl)ethyl(methyl)carbamate from Example 16A for (1S,2R)-1-amino-2-hydroxyindane in Example 13. The crude product was purified by reverse phase HPLC with acetonitrile/water to provide the desired product. MS (ESI) m/e 385 (M+H)$^+$; $^1$H NMR (300 MHz, DMSO-d$_6$) δ 10.17 (br s, 1H), 9.8 (br s, 1H), 8.28 (d, 1H), 8.08–7.95 (m, 4H), 7.7–7.55 (m, 3H), 6.56 (d, 1H), 5.63 (br s, 1H), 4.69 (dd, 1H), 4.57 (dd, 1H), 4.3 (m, 1H), 3.5 (br s, 1H), 2.6 (s, 3H), 1.7–1.5 (m, 6H), 1.45–1.35 (m, 3H), 1.22–1.05 (m, 3H), 0.88–0.73 (m, 1H).

EXAMPLE 20

(2R)-2-(methylamino)-2-(1-naphthyl)ethyl (2S,3R)-3-amino-2-hydroxy-5-phenylpentanoate The desired compound was obtained by substituting tert-butyl (1R)-2-hydroxy-1-(1-naphthyl)ethyl(methyl)carbamate from Example 16A and Example 6A for (1S,2R)-1-amino-2-hydroxyindane and Example 3C, respectively, in Example 13. The crude product was purified by reverse phase HPLC to provide the desired product. MS (ESI) m/e 393 (M+H)$^+$; $^1$H NMR (300 MHz, DMSO-d$_6$) δ 10.2 (br s, 1H), 9.8 (br s, 1H), 8.29 (d, 1H), 8.15 (br s, 2H), 8.04 (m, 3H), 7.7–7.58 (m, 3H), 7.34–7.16 (m, 4H), 6.63 (d, 1H), 5.63 (br s, 1H), 4.7–4.56 (m, 2H), 4.48 (br s, 1H), 3.58 (br s, 1H), 2.78–2.53 (m, 2H), 2.6 (s, 3H), 1.95–1.75 (m, 2H).

EXAMPLE 21 methyl (2RS,3R)-3-amino-5-(ethylsulfanyl)-2-hydroxypentanoate

EXAMPLE 21A methyl (2RS,3R)-3-[(tert-butoxycarbonyl)amino]-5-(ethylsulfanyl)-2-hydroxypentanoate The desired product was prepared by substituting Example 7B and diazomethane for Example 3C and trimethylsilyldiazomethane, respectively, in Example 12A.

EXAMPLE 21B methyl (2RS,3R)-3-amino-5-(ethylsulfanyl)-2-hydroxypentanoate

The desired product was prepared by substituting Example 21A for Example 3C in Example 3D. MS (ESI) m/e 208 (M+H)$^+$; $^1$H NMR (300 MHz, DMSO-d$_6$) δ 8.15 (br s, 0.6H), 7.99 (br s, 1.4H), 6.53 (d, 0.7H), 6.39 (d, 0.3H), 4.48 (m, 0.3H), 4.29 (m, 0.7H), 3.70 (s, 2.1H), 3.53 (s, 0.9H), 2.63 (m, 2H), 2.49 (m, 2H), 1.90–1.80 (m, 2H), 1.20–1.14 (m, 3H).

EXAMPLE 22 benzyl (2RS,3R)-3-amino-5-(ethylsulfanyl)-2-hydroxypentanoate

EXAMPLE 22A 3-tert-butyl 5-methyl (4R,5RS)-4-[2-(ethylsulfanyl)ethyl]-2,2-dimethyl-1,3-oxazolidine-3,5-dicarboxylate A mixture of Example 21A (1.12 g, 3.65 mmol) and catalytic 4-methylbenzenesulfonic acid (15 mg) in 2,2-dimethoxypropane (35 mL) at ambient temperature was stirred for 36 hours, diluted with ethyl acetate, washed sequentially with aqueous NaHCO$_3$ and pH 7 buffer, dried (MgSO$_4$), filtered, and concentrated. Flash column chromatography (silica gel, 10% acetone/hexanes) provided the desired product. MS (ESI) m/e 348 (M+H)$^+$.

EXAMPLE 22B (4R, 5RS)-3-(tert-butoxycarbonyl)-4-[2-(ethylsulfanyl)ethyl]-2,2-dimethyl-1,3-oxazolidine-5-carboxylic acid A 0° C. solution of Example 22A (0.65 g, 1.87 mmol) in THF (6 mL) was treated with a solution of lithium hydroxide monohydrate (0.088 g, 2.1 mmol) in water (2 mL), stirred for 2 hours, concentrated, and diluted with water. The aqueous phase was washed with diethyl ether, adjusted to pH 4 with 0.5M citric acid, and extracted twice with ethyl acetate. The combined extracts were dried (Na$_2$SO$_4$), filtered, and concentrated to provide the desired product. MS (ESI) m/e 334 (M+H)$^+$.

EXAMPLE 22C benzyl (2RS,3R)-3-amino-5-(ethylsulfanyl)-2-hydroxypentanoate

A solution of Example 22B (0.11 g, 0.33 mmol), benzyl alcohol (0.07 mL, 0.7 mmol), 1-(3-dimethylaminopropyl)-3-ethylcarbodiimide hydrochloride (0.080 g, 0.41 mmol), HOAT (0.045 g, 0.33 mmol), and N-methylmorpholine (0.055 mL, 0.50 mmol) in 3:1 dichloromethane/DMF (4 mL) at room temperature was stirred for 16 hours, diluted with dichloromethane, washed sequentially with aqueous NaHCO$_3$, brine, 0.5M citric acid, and brine, dried (MgSO$_4$), filtered, and concentrated. The residue was dissolved in 4M HCl in dioxane (2 mL), stirred for 1 hour, treated with water (1 mL), stirred for 1 hour, concentrated, and purified by reverse phase HPLC with acetonitrile/water to provide the desired product. MS (ESI) m/e 284 (M+H)$^+$; $^1$H NMR (300 MHz, DMSO-d$_6$) δ 7.43–7.37 (m, 5H), 5.20 (s, 1.4H), 5.19 (m, 0.6H), 4.44 (m, 0.3H), 4.32 (m, 0.7H), 3.53 (m, 1H), 2.63 (m, 2H), 2.43 (m, 2H), 1.90–1.75 (m, 2H), 1.20–1.12 (m, 3H).

EXAMPLE 23 butyl (2RS,3R)-3-amino-5-(ethylsulfanyl)-2-hydroxypentanoate

The desired product was prepared by substituting 1-butanol for benzyl alcohol in Example 22C. MS (ESI) m/e 250 (M+H)$^+$; $^1$H NMR (300 MHz, DMSO-d$_6$) δ 7.87–7.80 (br s, 2H), 6.53 (m, 0.7H), 6.33 (d, 0.3H), 4.40 (m, 0.3H), 4.24 (m, 0.7H), 4.12 (t, 2H), 3.53 (m, 1H), 2.63 (m, 2H), 2.48 (m, 2H), 1.90–1.75 (m, 2H), 1.66–1.57 (m, 2H), 1.44–1.33 (m, 2H), 1.22–1.16 (m, 3H) 0.92 (t, 3H).

EXAMPLE 24 isopropyl (2S,3R)-3-amino-2-hydroxy-5-(isopropylsulfanyl)pentanoate

The desired product was prepared by substituting 2-propanol and Example 7B for (1S,2R)-1-amino-2-hydroxyindane and Example 3C, respectively, in Example 13. The crude product was purified by reverse phase HPLC with acetonitrile/water to provide the desired product. MS (ESI)

m/e 250 (M+H)$^+$; $^1$H NMR (300 MHz, DMSO-d$_6$) δ 7.97 (br s, 2H), 6.62 (d, 1H), 5.02–4.92 (m, 1H), 4.18 (t, 1H), 3.73–3.63 (m, 1H), 3.53–3.38 (m, 2H), 2.98–2.85 (m, 1H), 2.7–2.55 (m, 1H), 1.8 (q, 1H), 1.25 (d, 6H), 1.2 (d, 6H).

EXAMPLE 25 isopropyl (2RS,3R)-3-amino-5-(ethylsulfanyl)-2-hydroxypentanoate

The desired product was prepared by substituting 2-propanol for benzyl alcohol in Example 22C. MS (ESI) m/e 236 (M+H)$^+$; $^1$H NMR (300 MHz, DMSO-d$_6$) δ 7.73 (br s, 2H), 4.97 (m, 1H), 4.15 (d, 1H), 3.44 (m, 1H), 2.63 (m, 2H), 2.49 (m, 2H), 1.79 (m, 2H), 1.23 (d, 6H), 1.18 (m, 3H).

EXAMPLE 26

[(2,2-dimethylpropanoyl)oxy]methyl (2RS,3R)-3-amino-5-(ethylsulfanyl)-2-hydroxypentanoate A solution of Example 22B (0.102 g, 0.31 mmol), cesium carbonate (0.111 g, 0.34 mmol), and chloromethyl pivalate (0.055 mL, 0.38 mmol) in DMF (3 mL) at room temperature was stirred for 24 hours, diluted with ethyl acetate, washed sequentially with water, aqueous NaHCO$_3$, pH 7 buffer, and brine, dried (MgSO$_4$), filtered, and concentrated. The residue was dissolved in 4M HCl in dioxane (2 mL), stirred for 1 hour, treated with water (1 mL), stirred for 1 hour, concentrated, and purified by reverse phase HPLC with acetonitrile/water to provide the desired product. MS (ESI) m/e 308 (M+H)$^+$; $^1$H NMR (300 MHz, DMSO-d$_6$) δ 7.87–7.80 (br s, 2H), 6.53 (m, 0.7H), 6.33 (d, 0.3H), 4.40 (m, 0.3H), 4.24 (m, 0.7H), 4.28 (s, 0.6H), 4.26 (s, 1.4H), 3.53 (m, 1H), 2.63 (m, 2H), 2.48 (m, 2H), 1.90–1.75 (m, 2H), 1.22–1.16 (m, 12H).

EXAMPLE 27 sec-butyl (2RS,3R)-3-amino-5-(ethylsulfanyl)-2-hydroxypentanoate

The desired product was prepared by substituting 2-butanol for benzyl alcohol in Example 22C. MS (ESI) m/e 250 (M+H)$^+$; $^1$H NMR (300 MHz, DMSO-d$_6$) δ 7.87–7.80 (br s, 2H), 6.53 (m, 0.7H), 6.33 (d, 0.3H), 4.83 (m, 1H), 4.40 (m, 0.3H), 4.24 (m, 0.7H), 3.53 (m, 1H), 2.63 (m, 2H), 2.48 (m, 2H), 1.90–1.75 (m, 2H), 1.28–1.17 (m, 7H), 0.92–0.84 (m, 3H).

EXAMPLE 28

(1,3-dioxo-1,3-dihydro-2H-isoindol-2-yl)methyl (2RS,3R)-3-amino-5-(ethylsulfanyl)-2-hydroxypentanoate The desired product was prepared by substituting N-(bromomethyl)phthalimide for chloromethyl pivalate in Example 26. MS (ESI) m/e 353 (M+H)$^+$; $^1$H NMR (300 MHz, DMSO-d$_6$) δ 7.99–7.82 (m, 4H), 6.64 (d, 0.7H), 6.48 (d, 0.3H), 5.73 (s, 1H), 4.97 (s, 1H), 4.30 (m, 0.7H), 4.18 (m, 0.3H), 3.53 (m, 1H), 2.63 (m, 2H), 2.48 (m, 2H), 1.90–1.75 (m, 2H), 1.22–1.16 (m, 3H).

EXAMPLE 29 sec-butyl (2RS,3R)-3-amino-2-hydroxy-5-(isopropylsulfanyl)pentanoate

EXAMPLE 29A (4R, 5RS)-3-(tert-butoxycarbonyl)-4-[2-(isopropylsulfanyl)ethyl]-2,2-dimethyl-1,3-oxazolidine-5-carboxylic acid The desired product was prepared by substituting Example 7B for Example 21A in Examples 22A and 22B.

EXAMPLE 29B sec-butyl (2RS,3R)-3-amino-2-hydroxy-5-(isopropylsulfanyl)pentanoate The desired product was prepared by substituting 2-butanol and Example 29A for benzyl alcohol and Example 22B, respectively, in Example 22C. MS (ESI) m/e 264 (M+H)$^+$; $^1$H NMR (300 MHz, DMSO-d$_6$) δ 7.97 (br s, 2H), 6.60–5.55 (m, 1H), 4.83 (m, 1H), 4.18 (m, 1H), 3.73–3.63 (m, 1H), 3.53–3.38 (m, 2H), 2.98–2.85 (m, 1H), 2.70–2.55 (m, 1H), 1.87–1.78 (m, 3H), 1.25 (m, 3H), 1.20 (d, 6H), 0.89–0.83 (m, 3H).

EXAMPLE 30

[(2,2-dimethylpropanoyl)oxy]methyl (2S,3R)-3-amino-2-hydroxy-5-(isopropylsulfanyl)pentanoate The desired product was prepared by substituting Example 29A for Example 22B in Example 26. The crude product was purified by reverse phase HPLC with acetonitrile/water to provide the desired product. MS (ESI) m/e 322 (M+H)$^+$; $^1$H NMR (300 MHz, DMSO-d$_6$) δ 7.97–7.83 (br m, 2H), 6.73 (d, 1H), 5.78 (dd, 2H), 4.33 (t, 1H), 4.16 (m, 1H), 3.73–3.63 (m, 1H), 3.53–3.38 (m, 1H), 2.98–2.85 (m, 1H), 2.70–2.55 (m, 1H), 1.87–1.78 (m, 1H), 1.20 (d, 6H), 1.12 (s, 9H).

EXAMPLE 31

(1,3-dioxo-1,3-dihydro-2H-isoindol-2-yl)methyl (2S,3R)-3-amino-2-hydroxy-5-(isopropylsulfanyl)pentanoate The desired product was prepared by substituting N-(bromomethyl)phthalimide and Example 29A for chloromethyl pivalate and Example 22B, respectively, in Example 26. The crude product was purified by reverse phase HPLC with acetonitrile/water to provide the desired product. MS (ESI) m/e 367 (M+H)$^+$; $^1$H NMR (300 MHz, DMSO-d$_6$) δ 7.97–7.83 (m, 6H), 6.63 (d, 1H), 5.72 (s, 1H), 4.97 (s, 1H), 4.32 (t, 1H), 4.17 (m, 1H), 3.73–3.63 (m, 1H), 3.53–3.38 (m, 1H), 2.98–2.85 (m, 1H), 2.70–2.55 (m, 1H), 1.87–1.78 (m, 1H), 1.20 (d, 6H).

EXAMPLE 32

3-oxo-1,3-dihydro-2-benzofuran-1-yl (2S,3R)-3-amino-2-hydroxy-5-(isopropylsulfanyl)pentanoate The desired product was prepared by substituting 3-bromophthalide and Example 29A for chloromethyl pivalate and Example 22B, respectively, in Example 26. The crude product was purified by reverse phase HPLC with acetonitrile/water to provide the desired product. MS (ESI) m/e 340 (M+H)$^+$; $^1$H NMR (300 MHz, DMSO-$d_6$) δ 8.03–7.92 (m, 3H), 7.83–7.78 (m, 2H), 7.66 (d, 1H), 6.63 (s, 1H), 4.28 (m, 1H), 4.18 (d, 1H), 3.73–3.63 (m, 1H), 3.53–3.38 (m, 1H), 2.98–2.85 (m, 1H), 2.70–2.55 (m, 1H), 1.87–1.78 (m, 1H), 1.20 (d, 6H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

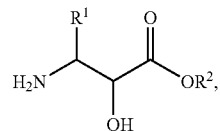

or a therapeutically acceptable salt thereof, wherein
  $R^1$ is hydroxyalkyl; and
  $R^2$ is selected from the group consisting of hydrogen, alkenyl, alkyl, alkylcarbonyloxyalkyl, alkylcarbonylalkyl, aryl, arylalkyl, cycloalkyl and (cycloalkyl)alkyl.

2. The compound of claim 1 wherein $R^2$ is hydrogen.

3. The compound of claim 1 which is (2S,3R,4S)-3-amino-2-hydroxy-4-(3-hydroxypropyl)-7-methyloctanoic acid.

4. A pharmaceutical composition comprising a compound of claim 1, or a therapeutically acceptable salt thereof, in combination with a therapeutically acceptable carrier.

* * * * *